(12) United States Patent
Sada et al.

(10) Patent No.: US 8,399,380 B2
(45) Date of Patent: Mar. 19, 2013

(54) HERBICIDAL COMPOSITION

(75) Inventors: Yoshinao Sada, Funabashi (JP); Satoru Kizawa, Kakogawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 65 days.

(21) Appl. No.: 12/739,903

(22) PCT Filed: Oct. 30, 2007

(86) PCT No.: PCT/JP2007/071461
§ 371 (c)(1),
(2), (4) Date: Apr. 26, 2010

(87) PCT Pub. No.: WO2009/057227
PCT Pub. Date: May 7, 2009

(65) Prior Publication Data
US 2010/0255993 A1    Oct. 7, 2010

(51) Int. Cl.
*A01N 43/40* (2006.01)
*A01N 43/48* (2006.01)
*A01N 43/84* (2006.01)
*A01P 13/00* (2006.01)

(52) U.S. Cl. ........ 504/130; 504/118; 504/134; 504/136; 504/140; 504/143; 514/230.05

(58) Field of Classification Search .......... 504/130, 504/118, 134, 136, 140, 143; 514/230.5
See application file for complete search history.

(56) References Cited

U.S. PATENT DOCUMENTS

| | | | |
|---|---|---|---|
| 4,994,102 A * | 2/1991 | Yoshido et al. | 504/128 |
| 6,211,118 B1 * | 4/2001 | Hoshi | 504/134 |
| 2002/0004457 A1 | 1/2002 | Nevill et al. | |
| 2006/0058192 A1 | 3/2006 | Kotzian | |

FOREIGN PATENT DOCUMENTS

| | | |
|---|---|---|
| JP | 61-76486 A | 4/1986 |
| JP | 3-000226 A | 1/1991 |
| JP | 2006-507354 A | 3/2006 |
| JP | 2006-520347 A | 9/2006 |
| JP | 2006-306730 A | 11/2006 |
| WO | 03/047343 A1 | 6/2003 |
| WO | 2004/080172 A2 | 9/2004 |

* cited by examiner

*Primary Examiner* — John Pak
*Assistant Examiner* — Andriae M Holt
(74) *Attorney, Agent, or Firm* — Sughrue Mion, PLLC

(57) ABSTRACT

A herbicidal composition for controlling weeds in orchard lands or non-crop lands which comprises (a) N-(7-fluoro-3,4-dihydro-3-oxo-4-prop-2-ynyl-2H-1,4-benzeoxazin-6-yl)cyclohex-1-ene-1,2-dicarboxamide and (b) 1-(4,6-dimethoxypyrimidin-2-yl)-3-(2-ethylsulfonylimidazo[1,2-a]pyridin-3-ylsulfonyl)urea as active ingredients, and a mixing ratio (the weight ratio of the active ingredient (a) to the active ingredient (b) of which is from 1:0.1 to 10.

2 Claims, No Drawings

HERBICIDAL COMPOSITION

TECHNICAL FIELD

The present invention relates to a herbicidal composition, and the like.

BACKGROUND ART

Nowadays, a herbicide, which has higher herbicidal activity and a broad herbicidal spectrum, and also has a long term effect and does not cause a phytotoxicity problem to crops, has been required.

DISCLOSURE OF THE INVENTION

An object of the present invention is to provide a technique which has a higher herbicidal activity and controls a broad range of weeds without causing a phytotoxicity problem to useful plants, for example, trees in orchard lands.

Under these circumstances, the present inventors have intensively studied, and have accomplished the present invention.

The present invention provides:

1. a herbicidal composition for controlling weeds in orchard lands or non-crop lands which comprises (a) N-(7-fluoro-3,4-dihydro-3-oxo-4-prop-2-ynyl-2H-1,4-benzeoxazin-6-yl)cyclohex-1-ene-1,2-dicarboxamide and (b) 1-(4,6-dimethoxypyrimidin-2-yl)-3-(2-ethylsulfonylimidazo[1,2-a]pyridin-3-ylsulfonyl)urea as active ingredients, and a mixing ratio (the weight ratio of the active ingredient (a) to the active ingredient (b)) of which is from 1:0.1 to 10 (hereinafter also referred to as composition of the present invention);

2. a method for controlling weeds in orchard lands or non-crop lands which comprises applying the herbicidal composition according to claim 1, or applying a combination of (a) N-(7-fluoro-3,4-dihydro-3-oxo-4-prop-2-ynyl-2H-1,4-benzeoxazin-6-yl)cyclohex-1-ene-1,2-dicarboxamide simultaneously with or in combination with (b) 1-(4,6-dimethoxypyrimidin-2-yl)-3-(2-ethylsulfonylimidazo[1,2-a]pyridin-3-ylsulfonyl)urea in a mixing ratio (the weight ratio of the active ingredient (a) to the active ingredient (b)) within a range from 1:0.1 to 10 to a soil where weeds are growing or where weeds are to grow, or weeds (hereinafter also referred to as composition of the present invention); and 3. use of a combination of (a) N-(7-fluoro-3,4-dihydro-3-oxo-4-prop-2-ynyl-2H-1,4-benzeoxazin-6-yl)cyclohex-1-ene-1,2-dicarboxamide and (b) 1-(4,6-dimethoxypyrimidin-2-yl)-3-(2-ethylsulfonylimidazo[1,2-a]pyridin-3-ylsulfonyl)urea in a mixing ratio (the weight ratio of the active ingredient (a) to the active ingredient (b)) within a range from 1:0.1 to 10 as active ingredients of a herbicidal composition for controlling weeds in orchard lands or non-crop lands (hereinafter also referred to as composition of the present invention).

N-(7-fluoro-3,4-dihydro-3-oxo-4-prop-2-ynyl-2H-1,4-benzeoxazin-6-yl)cyclohex-1-ene-1,2-dicarboxamide (generic name: flumioxazin, hereinafter also referred to as flumioxazin) used as an active ingredient in the composition of the present invention is a herbicidally active compound described in Crop Protection Handbook, Vol. 89 (2003), Meister Publishing Company, ISBN: 1-892829-06-1), page C236.

1-(4,6-dimethoxypyrimidin-2-yl)-3-(2-ethylsulfonylimidazo[1,2-a]pyridin-3-ylsulfonyl)urea (generic name: sulfosulfuron, hereinafter also referred to as sulfosulfuron) used as an active ingredient in the composition of the present invention is a herbicidally active compound described in Crop Protection Handbook, Vol. 89 (2003), Meister Publishing Company, ISBN: 1-892829-06-1), page C434.

The composition of the present invention has the herbicidal activity to a broad range of weeds and can effectively control a broad range of weeds in orchard lands and non-crop lands, and does not cause a problematic phytotoxicity to useful plants.

The orchard lands in the present invention mean lands where trees grow, such as orchards where fruit trees are cultured. The fruit trees include pomaceous fruits such as apple, pear, common pear, Chinese quince and quince; stone fruits such as peach, prune, plum, nectarine, apricot, Japanese apricot and yellow peach; grapes such as American grape and European grape; citrus fruits such as orange, mandarin orange, lemon, lime and grapefruit; nuts such as chestnut, walnut, hazel nut, almond, pistachio, cashew nut and *macadamia* nut; berry fruits such as blueberry, cranberry, blackberry and raspberry; Japanese persimmon; fig; loquat; olive; date palm; oil palm; banana; coffee; and mulberry. Trees other than the fruit trees include evergreen broad-leaved trees such as camphor tree, sasanqua, tea plant, camellia, eucalyptus and oleander; deciduous broad-leaved trees such as Japanese ash, birch, dogwood, ginkgo, lilac, maple tree, oak, poplar, Judas tree, sweetgum, platanus and zelkova; and acicular trees such as Japanese arborvitae, fir tree, Japanese hemlock, needle juniper, pine, spruce and Japanese yew.

The non-crop lands in the present invention include athletic ground, vacant land, railway side, park, parking lot, roadside, riverbed, vacant land under power transmission line, residential land, plant site and the like.

Weeds which can be controlled by the composition of the present invention include as follows.

Polygonaceae: *Polygonum convolvulus, Polygonum lapathifolium, Polygonum pensylvanicum, Polygonum persicaria, Rumex crispus, Rumex obtusifolius, Polygonum cuspidatum*

Portulacaceae: *Portulaca oleracea*

Caryophyllaceae: *Stellaria media*

Chenopodiaceae: *Chenopodium album, Kochia scoparia*

Amaranthaceae: *Amaranthus retroflexus, Amaranthus hybridus*

Brassicaceae: *Raphanus raphanistrum, Sinapis arvensis, Capsella bursa-pastoris*

Leguminosae: *Sesbania exaltata, Cassia obtusifolia, Desmodium tortuosum, Trifolium repens*

Malvaceae: *Abutilon theophrasti, Sida spinosa*

Violaceae: *Viola arvensis, Viola tricolor*

Rubiaceae: *Galium aparine*

Convolvulaceae: *Ipomoea hederacea, Ipomoea purpurea, Ipomoea hederacea* var *integriuscula, Ipomoea lacunosa, Convolvulus arvensis*

Lamiaceae: *Lamium purpureum, Lamium amplexicaule*

Solanaceae: *Datura stramonium, Solanum nigrum*

Scrophulariaceae: *Veronica persica, Veronica hederaefolia*

Asteraceae: *Xanthium pensylvanicum, Helianthus annuus, Matricaria inodora, Chrysanthemum segetum, Matricaria matricarioides, Ambrosia artemisiifolia, Ambrosia trifida, Erigeron canadensis, Artemisia princeps, Solidago altissima*

Boraginaceae: *Myosotis arvensis*

Asclepiadaceae: *Asclepias syriaca*

Euphorbiaceae: *Euphorbia helioscopia, Euphorbia maculata*

Poaceae: *Echinochloa crus-galli, Setaria viridis, Setaria faberi, Digitaria sanguinalis, Eleusine indica, Poa annua, Alopecurus myosuroides, Avena fatua, Sorghum halepense, Agropyron repens, Bromus tectorum, Cyn-* odone dactylon, Panicum dichotomiflorum, Panicum texanum, Sorghum vulgare, Lolium multiflorum
Commelinaceae: *Commelina communis, Commelina benghalensis*
Equisetaceae: *Equisetum arvense*
Cyperaceae: *Cyperus iria, Cyperus rotundus, Cyperus esculentus*

In the composition of the present invention, a mixing ratio of flumioxazin and sulfosulfuron used as active ingredients is within a range from 1:0.1 to 10, preferably from 1:0.2 to 5, and more preferably from 1:1/3 to 4.

The composition of the present invention may be usually used after mixing with solid carries or liquid carries, optionally adding surfactants or other adjuvants for formulation and formulating the resultant mixture into emulsifiable concentrates, wettable powders, suspension concentrates and granules. These formulations may contain flumioxazin and sulfosulfuron in the total amount of about 0.1 to 90% by weight, and preferably about 1 to 80% by weight.

Solid carries used to formulate the composition of the present invention include, for example, finely-divided powders or granules of clay (kaolinite, diatomaceous earth, synthetic water-containing silicon oxide, Fubasami clay, bentonite, acid clay, etc.), talc, other inorganic minerals (sericite, quartz powder, sulfur powder, activated carbon, calcium carbonate, etc.) and chemical fertilizers (ammonium sulfate, ammonium phosphate, ammonium nitrate, ammonium chloride, urea, etc.). Liquid carries include, for example, water, alcohols (methanol, ethanol, etc.), ketones (acetone, methyl ethyl ketone, cyclohexanone, etc.), aromatic hydrocarbons (toluene, xylene, ethylbenzene, methylnaphthalene, etc.), non-aromatic hydrocarbons (hexane, cyclohexane, kerosene, etc.), esters (ethyl acetate, butyl acetate, etc.), nitriles (acetonitrile, isobutyronitrile etc.), ethers (dioxane, diisopropylether, etc.), acid amides (dimethylformamide, dimethylacetamide, etc.) and halogenated hydrocarbons (dichloromethane, trichloroethane, etc.).

The composition of the present invention can also be prepared by mixing each formulation after individually formulating each of active ingredients using the above formulation technique.

The thus formulated composition of the present invention may be directly applied to the soil or plants or may be applied thereto after diluting with water or the like to obtain a dilution. Furthermore, enhancement of the herbicidal activity can be expected by mixing the composition of the present invention with other herbicides. It is also possible to use in combination with insecticides, fungicides, plant growth regulators, fertilizers, safeners, soil conditioners and the like.

Although the application amount of the composition of the present invention can vary depending on a mixing ratio of flumioxazin and sulfosulfuron as active ingredients, climate conditions, form of formulations, application time, application method, application area, weeds to be controlled and crops, the total amount of the active ingredient compounds is usually from about 1 to 1,000 g per hectare. The emulsifiable concentrate, wettable powder, suspension concentrate or the like is usually applied after diluting the predetermined amount thereof with about 100 to 20,000 liters of water per hectare. When the composition of the present is applied to weeds by foliar application, enhancement of the efficacy against weeds can be expected by adding adjuvants to the dilution of the composition of the present invention.

EXAMPLES

The present invention will be described in detail by way of examples, but the present invention is not limited to these Examples.

Formulation examples are shown below. In the examples, parts are by weight.

Formulation Example 1

Wettable powders are obtained by sufficiently grinding and mixing 25 parts of flumioxazin, 25 parts of sulfosulfuron, 3 parts of calcium lignin sulfonate, 2 parts of sodium lauryl sulfate and 45 parts of synthetic water-containing silicon oxide.

Formulation Example 2

Wettable powders are obtained by sufficiently grinding and mixing 70 parts of flumioxazin, 14 parts of sulfosulfuron, 3 parts of calcium lignin sulfonate, 2 parts of sodium lauryl sulfate and 11 parts of synthetic water-containing silicon oxide.

Formulation Example 3

Wettable powders are obtained by sufficiently grinding and mixing 14 parts of flumioxazin, 70 parts of sulfosulfuron, 3 parts of calcium lignin sulfonate, 2 parts of sodium lauryl sulfate and 11 parts of synthetic water-containing silicon oxide.

Formulation Example 4

Wettable powders are obtained by sufficiently grinding and mixing 10 parts of flumioxazin, 5 parts of sulfosulfuron, 3 parts of calcium lignin sulfonate, 2 parts of sodium lauryl sulfate and 80 parts of synthetic water-containing silicon oxide.

Formulation Example 5

Suspensions are obtained by mixing 20 parts of flumioxazin, 20 parts of sulfosulfuron, 3 parts of polyoxyethylene sorbitan monoleate, 3 parts of CMC (carboxymethyl cellulose) and 54 parts of water, and wet-grinding the resultant mixture so as to adjust the particle size to 5 micron or less.

Formulation Example 6

Suspensions are obtained by mixing 50 parts of flumioxazin, 10 parts of sulfosulfuron, 3 parts of polyoxyethylene sorbitan monoleate, 3 parts of CMC (carboxymethyl cellulose) and 34 parts of water, and wet-grinding the resultant mixture so as to adjust the particle size to 5 micron or less.

Formulation Example 7

Suspensions are obtained by mixing 5 parts of flumioxazin, 25 parts of sulfosulfuron, 3 parts of polyoxyethylene sorbitan monoleate, 3 parts of CMC (carboxymethyl cellulose) and 64 parts of water, and wet-grinding the resultant mixture so as to adjust the particle size to 5 micron or less.

Formulation Example 8

Suspensions are obtained by mixing 4 parts of flumioxazin, 2 parts of sulfosulfuron, 3 parts of polyoxyethylene sorbitan monoleate, 3 parts of CMC (carboxymethyl cellulose) and 88 parts of water, and wet-grinding the resultant mixture so as to adjust the particle size to 5 micron or less.

Biological test examples are shown below.

Evaluation Criteria

The herbicidal activity is evaluated at 6 levels using the indices of 0 to 5, i.e., shown by "0", "1", "2", "3", "4" or "5", wherein a score of "0" means that there is no or little difference in the degree of growth between treated plants and untreated plants at the time of observation and a score of "5" means that the test plants die completely or their growth is completely inhibited. The herbicidal values of "4" and "5" show excellent herbicidal activity.

The phytotoxicity is evaluated at 4 levels using "no damage", "small", "medium" or "severe", wherein "no damage" means that no damage is found or the damage practically causes no problem, "small" means that the damage is light but practically impermissible, "medium" means that the damage is medium and "severe" means that severe damage is found.

Test Example 1

Soil Application

Each of plastic pots (measuring 22 cm in diameter and 19 cm in height) was filled with upland field soil and sown with Lolium multiflorum and Alopecurus myosuroides. Each of the predetermined amounts of a flumioxazin formulation product (trade name: Valor_SX, manufactured by Valent USA Corporation), a sulfosulfuron formulation product (trade name: Monitor, manufactured by Monsanto Company) and a mixture of the flumioxazin formulation product and the sulfosulfuron formulation product was diluted with water, and then the dilution was uniformly sprayed over the soil surface by a small-sized sprayer. After the treatment, the weeds were grown in a greenhouse, and the herbicidal activity against the weeds was evaluated at 34 days after application. The results are shown in Table 1.

TABLE 1

| Compounds under test | Amount of active ingredient (g/ha) | Herbicidal activity Lolium multiflorum | Herbicidal activity Alopecurus myosuroides |
|---|---|---|---|
| Flumioxazin | 10 | 0 | 1 |
| Flumioxazin | 20 | 1 | 4 |
| Sulfosulfuron | 20 | 0 | 0 |
| Sulfosulfuron | 40 | 0 | 2 |
| Flumioxazin + Sulfosulfuron | 10 + 20 | 2 | 5 |
| Flumioxazin + Sulfosulfuron | 10 + 40 | 2 | 5 |
| Flumioxazin + Sulfosulfuron | 20 + 20 | 5 | 5 |
| Flumioxazin + Sulfosulfuron | 20 + 40 | 4 | 5 |

Test Example 2

Foliar Application

Each of plastic pots (measuring 12 cm in diameter and 8 cm in height) was filled with upland field soil and Solidago altissima collected from outdoors was transplanted to the plastic pot and grown in a greenhouse for 31 days. Each of the predetermined amounts of a flumioxazin formulation product (trade name: Valor_SX, manufactured by Valent USA Corporation), a sulfosulfuron formulation product (trade name: Monitor, manufactured by Monsanto Company) and a mixture of the flumioxazin formulation product and the sulfosulfuron formulation product was diluted with water, and then the dilution was uniformly sprayed over each plant body from above by a small-sized sprayer. After the treatment, the weeds were grown in a greenhouse for 29 days, and then the herbicidal activity against the weeds was evaluated. The results are shown in Table 2.

TABLE 2

| Compounds under test | Amount of active ingredient (g/ha) | Herbicidal activity Solidago altissima |
|---|---|---|
| Flumioxazin | 60 | 0 |
| Flumioxazin | 120 | 1 |
| Sulfosulfuron | 40 | 2 |
| Flumioxazin + Sulfosulfuron | 60 + 40 | 5 |
| Flumioxazin + Sulfosulfuron | 120 + 40 | 5 |

As shown in the test examples described above, by either of the soil application and the foliar application, the herbicidal activity, which is excellent when compared with the flumioxazin spraying section or the sulfosulfuron spraying section, was obtained in the treatment section of the composition of the present invention.

Furthermore, the phytotoxicity to trees was examined in orchard lands where apple, Japanese pear, peach, Japanese persimmon, grape and citrus fruits are cultured, using the composition of the present invention. No phytotoxicity was recognized in all trees.

Test Example 3

In orchards where pear and mandarin orange are cultured, the predetermined amount of a mixture of a flumioxazin formulation product (trade name: Valor_SX, manufactured by Valent USA Corporation) and a sulfosulfuron formulation product (trade name: Monitor, manufactured by Monsanto Company) was diluted with water and then the dilution was uniformly sprayed over growing Ipomoea hederacea and Equisetum arvense from above by a carbon dioxide gas sprayer. Sixty-three days after the chemical treatment, the herbicidal activity against the weeds and phytotoxicity to the trees were examined. The results are shown in Table 3.

TABLE 3

| Compounds under test | Amount of active ingredient (g/ha) | Herbicidal activity Ipomoea hederacea | Herbicidal activity Equisetum arvense | Phytotoxicity Pear | Phytotoxicity mandarin orange |
|---|---|---|---|---|---|
| Flumioxazin + Sulfosulfuron | 50 + 50 | 5 | 5 | No injury | No injury |
| Flumioxazin + Sulfosulfuron | 50 + 500 | 5 | 5 | No injury | No injury |
| Flumioxazin + Sulfosulfuron | 500 + 50 | 5 | 5 | No injury | No injury |
| Flumioxazin + Sulfosulfuron | 500 + 500 | 5 | 5 | No injury | No injury |

Industrial Applicability

According to the present invention, the composition of the present invention can be applied in orchard lands or non-crop lands in a small amount, thus making it possible to control a broad range of weeds.

The invention claimed is:

1. A herbicidal composition for controlling weeds in orchard lands or non-crop lands which comprises (a) N-(7-fluoro-3,4-dihydro-3-oxo-4-prop-2-ynyl-2H-1,4-benzeoxazin-6-yl)cyclohex-1-ene-1,2-dicarboxamide and (b) 1-(4,6-dimethoxypyrimidin-2-yl)-3-(2-ethylsulfonylimidazo[1,2-a]pyridin-3-ylsulfonyl)urea as active ingredients, wherein the weight ratio of the active ingredient (a) to the active ingredient (b) is from 1:0.1 to 1:10.

2. A method for controlling weeds in orchard lands or non-crop lands which comprises applying the herbicidal composition according to claim 1, or applying a combination of (a) N-(7-fluoro-3,4-dihydro-3-oxo-4-prop-2-ynyl-2H-1,4-benzeoxazin-6-yl)cyclohex-1-ene-1,2-dicarboxamide simultaneously with or in combination with (b) 1-(4,6-dimethoxypyrimidin-2-yl)-3-(2-ethylsulfonylimidazo[1,2-a]pyridin-3-ylsulfonyl)urea, wherein the weight ratio of the active ingredient (a) to the active ingredient (b) is from 1:0.1 to 1:10 to a soil where weeds are growing or where weeds are to grow, or weeds.

* * * * *